United States Patent
O'Dea (10) Patent No.: US 9,808,179 B2
(45) Date of Patent: Nov. 7, 2017

(54) CATHETER AND A SYSTEM AND A METHOD FOR LOCATING A CATHETER IN A VESSEL

(75) Inventor: John O'Dea, Galway (IE)

(73) Assignee: Flip Technologies Limited, Galway (IE)

( * ) Notice: Subject to any disclaimer, the term of this patent is extended or adjusted under 35 U.S.C. 154(b) by 401 days.

(21) Appl. No.: 14/236,522

(22) PCT Filed: Aug. 3, 2012

(86) PCT No.: PCT/IE2012/000040
§ 371 (c)(1),
(2), (4) Date: Apr. 21, 2014

(87) PCT Pub. No.: WO2013/018079
PCT Pub. Date: Feb. 7, 2013

(65) Prior Publication Data
US 2014/0243640 A1 Aug. 28, 2014

(30) Foreign Application Priority Data
Aug. 3, 2011 (IE) .................................. S2011/0342

(51) Int. Cl.
*A61B 5/04* (2006.01)
*A61B 5/06* (2006.01)
(Continued)

(52) U.S. Cl.
CPC .............. *A61B 5/065* (2013.01); *A61B 1/051* (2013.01); *A61B 1/0684* (2013.01); *A61B 1/07* (2013.01);
(Continued)

(58) Field of Classification Search
CPC ..... A61B 5/065; A61B 5/6852; A61B 5/6853; A61B 5/6855; A61B 5/6856; A61B 5/6857; A61B 5/6859; A61B 18/1492
(Continued)

(56) References Cited

U.S. PATENT DOCUMENTS 4,567,882 A * 2/1986 Heller .................. A61M 25/01
128/200.26
4,785,815 A 11/1988 Cohen
(Continued)

FOREIGN PATENT DOCUMENTS

EP 0 893 101 A2 1/1999
EP 1 760 661 A2 3/2007
(Continued)

OTHER PUBLICATIONS

International Search Report of PCT/IE2012/000040 dated Nov. 16, 2012.

*Primary Examiner* — Lee S Cohen
(74) *Attorney, Agent, or Firm* — Sughrue Mion, PLLC (57) ABSTRACT

A balloon catheter (60) includes an elongated catheter member (63) and an inflatable balloon (65) located adjacent a distal end (5) of the catheter member (63). Band type measuring electrodes (7) located on the catheter member (63) within the balloon (65) include a pair of outer stimulating electrodes (8) and sensing electrodes (9) for measuring the cross-sectional area and volume of the balloon (65) by impedance planimetry measuring. A light emitting diode (20) is located on each measuring electrode (7) for emitting light so that the location of the balloon catheter, and in particular, the measuring electrodes (7) can be detected in a vessel (91) with a translucent wall within the body of a human subject. By capturing an image of the vessel and the light from the light emitting diodes (20) emanating through a translucent wall of the vessel by an imaging device (92)

(Continued)

located within the human body externally of the vessel (91), the location of the balloon catheter and the electrodes (7) within the vessel can be determined.

18 Claims, 6 Drawing Sheets

(51) Int. Cl.
| | |
|---|---|
| *A61B 5/00* | (2006.01) |
| *A61B 1/05* | (2006.01) |
| *A61B 1/06* | (2006.01) |
| *A61B 1/07* | (2006.01) |
| *A61B 1/313* | (2006.01) |
| *A61B 5/053* | (2006.01) |
| *A61B 5/107* | (2006.01) |
| *A61B 5/042* | (2006.01) |
| *A61M 25/01* | (2006.01) |
| *A61M 25/10* | (2013.01) |
| *A61B 18/14* | (2006.01) |
| *A61B 18/00* | (2006.01) |
| *A61B 34/20* | (2016.01) |

(52) U.S. Cl.
CPC .......... *A61B 1/3132* (2013.01); *A61B 5/0084* (2013.01); *A61B 5/0538* (2013.01); *A61B 5/064* (2013.01); *A61B 5/1076* (2013.01); *A61B 5/6853* (2013.01); *A61B 34/20* (2016.02); *A61M 25/1018* (2013.01); *A61B 5/0422* (2013.01); *A61B 5/061* (2013.01); *A61B 18/1492* (2013.01); *A61B 2018/0022* (2013.01); *A61B 2034/2055* (2016.02); *A61M 2025/0166* (2013.01); *A61M 2025/1086* (2013.01)

(58) Field of Classification Search
USPC .................................................. 600/373, 380
See application file for complete search history.

(56) References Cited

U.S. PATENT DOCUMENTS

| | | | | |
|---|---|---|---|---|
| 7,917,193 | B2* | 3/2011 | Crane .................. | A61B 5/0059 600/473 |
| 8,500,730 | B2* | 8/2013 | Lee ...................... | A61B 5/0084 606/41 |
| 8,613,702 | B2* | 12/2013 | Feer ..................... | A61B 5/0538 600/301 |
| 9,345,891 | B2* | 5/2016 | Thacker ............. | A61N 1/36071 |
| 2006/0184165 | A1* | 8/2006 | Webster, Jr. ........ | A61B 18/1492 606/41 |
| 2007/0287998 | A1* | 12/2007 | Sharareh ............ | A61B 18/1492 606/41 |
| 2008/0119694 | A1* | 5/2008 | Lee ...................... | A61B 5/0084 600/127 |
| 2010/0145178 | A1* | 6/2010 | Kartush ............... | A61B 5/4893 600/380 |
| 2010/0312094 | A1 | 12/2010 | Guttman et al. | |
| 2014/0243640 | A1* | 8/2014 | O'Dea ................. | A61B 5/0084 600/373 |

FOREIGN PATENT DOCUMENTS

| | | |
|---|---|---|
| WO | 2006/116748 A1 | 11/2006 |
| WO | 2009/001325 A1 | 12/2008 |
| WO | 2010/103502 A2 | 9/2010 |

\* cited by examiner

CATHETER AND A SYSTEM AND A METHOD FOR LOCATING A CATHETER IN A VESSEL

CROSS REFERENCE TO RELATED APPLICATIONS

This is a National Stage of International Application No. PCT/IE2012/000040 filed Aug. 3, 2012, claiming priority based on Irish Patent Application No. S2011/0342 filed Aug. 2, 2011, the contents of all of which are incorporated herein by reference in their entirety.

BACKGROUND OF THE INVENTION

The present invention relates to a catheter, and in particular, though not limited to a measuring catheter, such as, for example, a catheter having two or more measuring electrodes located at spaced apart intervals on the catheter or a balloon catheter comprising an elongated catheter having an inflatable element located on the catheter and two or more measuring electrodes located within the inflatable element on the catheter. The invention also relates to a system and a method for locating a catheter in a vessel in a human or animal subject.

Catheters for measuring cross-sectional area, diameter, as well as volume of a vessel in a human or animal body are well known. Such catheters may comprise an elongated catheter having two or more, and typically a plurality of measuring electrodes longitudinally spaced apart along the catheter towards a distal end thereof. Typically, two of the electrodes are stimulating electrodes to which a stimulating current of constant known value is applied, and the remaining electrodes which are located between the stimulating electrodes are sensing electrodes. When the portion of the catheter with the measuring electrodes thereon is located in a vessel, and the vessel is filled with an electrically conductive medium, voltages are induced on the sensing electrodes when the stimulating current is applied to the stimulating electrodes. The voltages induced on the sensing electrodes are indicative of the cross-sectional area and the diameter of the vessel adjacent the respective sensing electrodes. If the vessel is assumed to be of circular transverse cross-section, the voltage signal induced on the sensing electrodes are indicative of the diameter of the vessel. From these voltage values the cross-sectional area and the diameter of the vessel adjacent the respective sensing electrodes can be computed as well as the volume of the vessel. Typically, such catheters are used for measuring the diameter, cross-sectional area or volume of a relatively narrow vessel, such as, for example, an artery or the like.

Another type of measuring catheter is a balloon catheter which comprises an elongated catheter having an inflatable element, typically a balloon located on the catheter towards the distal end thereof, with the catheter extending through the balloon to define with the balloon an annular hollow interior region. Measuring electrodes similar to those described with reference to a measuring catheter are provided on the catheter within the balloon. Such balloon catheters are generally used for determining the cross-sectional area, diameter and the volume of a larger vessel in the human or animal body, for example, the stomach, the oesophagus, the rectum, intestine, the bowel or the like, and are also commonly used in procedures known as bariatric surgery as well as anti-reflux surgery to correct gastro-oesophageal reflux disease. To determine the diameter, cross-sectional area and/or volume of a vessel, the balloon of the balloon catheter is placed in the vessel, and the balloon is inflated with an electrically conductive inflating medium to fill the vessel. By applying a constant current of known value through the stimulating electrodes, voltages induced on the sensing electrodes are indicative of the diameter and cross-sectional area and the diameter of the vessel adjacent the respective sensing electrodes.

One problem which arises with such catheters, be they measuring catheters without a balloon or measuring catheters with a balloon, namely, balloon catheters, is that, in general, it is relatively difficult to locate the balloon, or in the case of a non-balloon catheter, the portion of the electrodes accurately in the vessel, the diameter, cross-sectional area or volume of which is to be determined, or monitored. For example, during bariatric surgery and anti-reflux surgery it is difficult to accurately locate the balloon of a balloon catheter in the stomach or the lower oesophageal sphincter, as the case may be, with the sensing electrodes accurately located relative to the lower oesophageal sphincter and the stomach.

Additionally, catheters and balloon catheters having one or more spaced apart ablating electrodes on the catheter of an ablating catheter, and on the external surface of the balloon in the case of an ablating balloon catheter, are used for ablating tissue in a lumen or vessel. It is also in many cases difficult to locate such catheters and balloon catheters in the vessel or lumen with the ablating electrodes accurately aligned with the tissue to be ablated.

There is therefore a need for a catheter and a balloon catheter which addresses these problems.

The present invention is directed towards providing such a catheter; the catheter may be a balloon catheter or a non-balloon catheter, and the invention is also directed towards providing a system and a method for locating a catheter, be it a balloon catheter or a non-balloon catheter, in a vessel.

SUMMARY OF THE INVENTION

According to the invention, there is provided a catheter comprising an elongated catheter member, at least two spaced apart electrodes, and an indicating means located adjacent at least one of the electrodes, the indicating means being adapted to output a detectable signal for identifying the location of the adjacent electrode.

In one aspect of the invention one indicating means is located adjacent each of at least some of the electrodes.

In another aspect of the invention each indicating means is located on the corresponding electrode.

In a further aspect of the invention each indicating means is located in the corresponding electrode.

In one embodiment of the invention each electrode is located on the catheter member, and in another embodiment of the invention each indicating means is located on the catheter member adjacent the corresponding electrode.

Preferably, the signal outputted by each indicating means is adapted to be receivable by an imaging device of an imaging system. Advantageously, the signal outputted by each indicating means is adapted to be receivable by a charge coupled device (CCD) imaging chip.

Alternatively, the signal outputted by each indicating means is adapted to be receivable by a digital video camera.

In one aspect of the invention the signal outputted by each indicating means is adapted to be receivable by an imaging device of an imaging system adapted for use in a laparoscopic procedure.

In another aspect of the invention the signal outputted by each indicating means comprises a light signal derived from a light source.

Preferably, each indicating means comprises a light outputting means.

In one aspect of the invention each light outputting means comprises an opening for accommodating light therethrough.

In another aspect of the invention each light outputting means comprises a lens for accommodating the light therethrough.

In a further aspect of the invention the light source comprises a remote light source, and a light transmitting means is provided for communicating the light outputting means with the remote light source.

Preferably, the light transmitting means extends through the catheter member. Advantageously, the light transmitting means extends from the proximal end of the catheter member. Preferably, the light transmitting means adjacent the proximal end of the catheter member is adapted for coupling to the remote light source.

Advantageously, at least two remote light sources are provided, and the light transmitting means is adapted for communicating the remote light sources to respective ones or respective groups of the light outputting means for transmitting light thereto from the respective remote light sources.

In one aspect of the invention the remote light sources produce light of respective different wavelengths.

Preferably, each remote light source comprises at least one light emitting diode. Advantageously, each remote light source comprises a plurality of light emitting diodes.

In one embodiment of the invention the light transmitting means comprises at least one optical fibre.

In another embodiment of the invention the light transmitting means comprises a plurality of optical fibres. Preferably, each optical fibre terminates in a distal end adjacent the corresponding light outputting means.

In another embodiment of the invention the light transmitting means comprises at least one elongated light accommodating bore extending through the catheter member for communicating the light outputting means with the remote light source. Preferably, a light directing means is located in each light accommodating bore adjacent a corresponding one of the light outputting means to which light is to be transmitted for directing light from the light accommodating bore to the corresponding light outputting means. Preferably, each light directing means comprises a reflector.

In another aspect of the invention a bore extends into the catheter member adjacent each electrode for communicating the corresponding light outputting means with the light transmitting means. Advantageously, each light outputting means communicates with the light transmitting means through a bore extending through the corresponding electrode.

In one aspect of the invention each indicating means comprises a corresponding light source. Preferably, the light source of each indicating means comprises a light emitting diode.

In another aspect of the invention at least some of the light sources of the respective indicating means produce light of respective different wavelengths.

In one embodiment of the invention at least some of the electrodes are adapted for measuring volume and/or transverse cross-sectional area of a vessel or a lumen in which the catheter is located, and two of the electrodes are located longitudinally spaced apart from each other on a distal portion of the catheter member and are adapted as stimulating electrodes for receiving a stimulating electrical current, and other ones of the electrodes are located on the catheter member between the stimulating electrodes longitudinally spaced apart from each other and from the stimulating electrodes, and are adapted as sensing electrodes for sensing a voltage developed thereon in response to a stimulating current being applied to the stimulating electrodes when the distal portion of the catheter member is located in an electrically conducted medium.

In another embodiment of the invention at least one of the electrodes is adapted for ablating tissue.

In another embodiment of the invention the catheter further comprises an inflatable balloon mounted on the catheter member, and a communicating means is provided for communicating the balloon with an inflating medium source.

Preferably, the communicating means is adapted for communicating the balloon with an electrically conductive medium source.

In one embodiment of the invention at least one of the electrodes is located on the balloon on an outer surface of the balloon.

In another embodiment of the invention one of the indicating means is located adjacent the electrode located on the balloon.

In one aspect of the invention at least two of the electrodes are located on the balloon on the outer surface thereof.

In another embodiment of the invention each electrode located on the balloon is adapted for ablating tissue.

Preferably, the balloon is located on the catheter member with at least some of the electrodes located on the catheter member within the balloon. Advantageously, the catheter member extends through the balloon. Preferably, the balloon defines with the catheter member an annular hollow interior region extending around the catheter member.

In one embodiment of the invention each electrode is provided with a corresponding indicating means.

In another embodiment of the invention each electrode comprises a band electrode.

The invention also provides a system for locating a catheter in a vessel or lumen in a human or animal subject, the system comprising the catheter according to the invention for locating in the vessel or lumen, and an imaging device for locating in the body of the subject adjacent the vessel or lumen but exteriorly thereof, the imaging device being adapted for capturing an image of the vessel or lumen and the indicating means of the catheter located within the vessel or lumen.

Preferably, the imaging device comprises a charge coupled device (CCD) imaging clip. Alternatively, the imaging device comprises a video camera.

In one embodiment of the invention the imaging device is adapted for use in a laparoscopic procedure.

The invention further provides a method for locating a catheter in a vessel or lumen of a human or animal subject, the catheter comprising a catheter member and at least two longitudinally spaced apart electrodes, the method comprising placing at least one indicating means adjacent at least one of the electrodes, and adapting the indicating means to output a detectable signal, placing a portion of the catheter member comprising the electrodes and the at least one indicating means in the vessel or lumen, placing an imaging device in the body of the subject adjacent the vessel or lumen but exteriorly thereof, causing the indicating means to output the detectable signal, and capturing an image of the vessel or lumen and the detectable signal for in turn detecting the location in the vessel or lumen of the electrode adjacent which the indicating means is located.

Preferably, the image captured by the imaging means is displayed on a visual display screen.

Preferably, the catheter member is manoeuvred within the vessel or lumen until the image of the vessel or lumen and the detectable signal outputted by the indicating means displayed on the visual display screen is indicative of the catheter member being correctly located in the vessel or lumen.

The advantages of the invention are many. A particularly important advantage of the invention is that the catheter and the balloon catheter as the case may be may be readily easily located in a vessel or lumen in which it is to be located with the electrodes thereof, be they measuring or ablating electrodes or both, or other types of electrodes, relatively accurately located in the vessel or lumen. This permits accurate computation of the cross-sectional area and/or diameter and/or volume of a vessel or lumen at a precise location. Relatively accurate alignment of ablating electrodes of such a catheter or balloon catheter with tissue to be ablated is also achieved.

The provision of the indicating means as an outputting means for outputting a light signal provides a significant advantage when the catheter or balloon catheter is being used in a vessel or lumen which is transparent or translucent, since an imaging device can be placed in the body of a subject externally of the vessel or lumen, and an image of the vessel or lumen can be captured by the imaging device, which also captures an image of the light being outputted by the light outputting means of the catheter or balloon catheter.

Since each light outputting means is located adjacent a corresponding one of the electrodes, the location of the respective electrodes can be readily easily identified from the captured image. Furthermore, the catheter or balloon catheter can be manoeuvred in the vessel or lumen, and images of the catheter or balloon catheter together with images of the light being outputted by the light outputting means can be captured while the catheter or balloon catheter is being manoeuvred in the vessel or lumen, thereby permitting accurate placement of the catheter or balloon catheter in the vessel or lumen.

BRIEF DESCRIPTION OF THE DRAWINGS

The invention will be more clearly understood from the following description of some preferred embodiments thereof, which are given by way of example only, with reference to the accompanying drawings, in which.

DETAILED DESCRIPTION OF THE INVENTION

Figure 1:
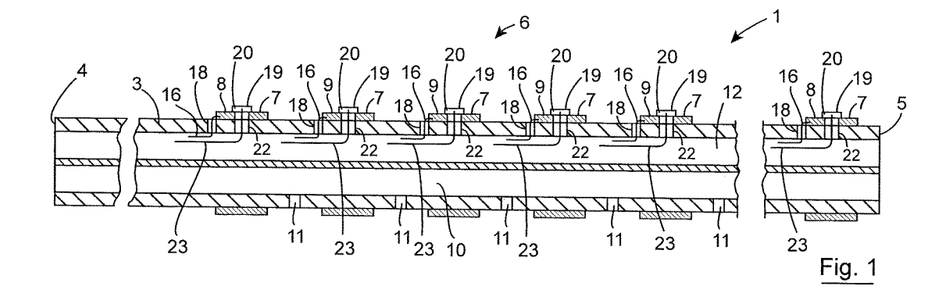
FIG. 1 is a longitudinal cross-sectional side elevational view of a catheter according to the invention.

Referring to the drawings and initially to FIG. 1, there is illustrated a catheter according to the invention, indicated generally by the reference numeral 1, for determining the diameter, the transverse cross-sectional area and/or the volume of a vessel, for example, an artery, a vessel in the heart or other organ or lumen in the body of a human or animal subject. The catheter 1 comprises an elongated catheter member 3 extending from a proximal end 4 to a distal end 5.

A plurality of electrodes, in this embodiment of the invention measuring electrodes 7 are located longitudinally spaced apart on a distal portion 6 of the catheter member 3 towards the distal end 5 thereof. The measuring electrodes 7 are band type electrodes of electrically conductive foil, which extend completely around the catheter member 3. Two of the measuring electrodes 7, namely, the outer two measuring electrodes 7 are provided as stimulating electrodes 8 for receiving a constant stimulating current signal of known value. The remaining measuring electrodes 7, namely, the measuring electrodes 7 which are located between the stimulating electrodes 8 are adapted as sensing electrodes 9 on which voltages are developed in response to the stimulating constant current signal being applied to the stimulating electrodes 8 when a vessel or lumen within which the distal portion 6 of the catheter member 3 is located is filled with an electrically conductive medium, typically a saline solution. The voltages which are developed on the sensing electrodes 9 are indicative of the values of the transverse cross-sectional area of the vessel or lumen adjacent the corresponding sensing electrodes 9. If the vessel or lumen within which the distal portion 6 of the catheter 1 is located is assumed to be of circular transverse cross-section, the voltages which are developed on the sensing electrodes 9 are indicative of the values of the diameter of the vessel or lumen adjacent the sensing electrodes. As will be known to those skilled in the art, the volume of the vessel between the stimulating electrodes 8 or between any two of the sensing electrodes 9 or between one of the stimulating electrodes 8 and one of the sensing electrodes 9 can be computed from the values of the cross-sectional area adjacent the relevant sensing electrodes 9 and the spacing between those sensing electrodes 9.

A communicating means, namely, an electrically conductive medium accommodating bore 10 extending longitudinally through the catheter member 3 from the proximal end 4 to the distal end 5 accommodates a saline solution being delivered into the vessel or lumen. Ports 11 extending radially through the catheter member 3 which communicate with the electrically conductive medium accommodating bore 10 accommodate the electrically conductive medium from the bore 10 into the vessel. Such catheters having measuring electrodes located thereon for determining the diameter, cross-sectional area and/or the volume of a vessel when the vessel is filled with an electrically conductive medium are known. A typical one of such catheters is disclosed in U.S. Pat. No. 4,840,182 of Carlson.

An elongated longitudinally extending cable accommodating bore 12 extends through the catheter member 3 from the proximal end 4 thereof towards the distal end 5 for accommodating mutually electrically insulated, electrically conductive wires 16 from the proximal end 4 to the stimulating electrodes 8 and the sensing electrodes 9. Two of the wires 16 which are connected to the stimulating electrodes 8 carry the constant current signal to and from the stimulating electrodes 8, while the voltages induced on the sensing electrodes 9 can be read from the wires 16 which are connected to the sensing electrodes 9. Wire accommodating bores 18 extending radially through the catheter member 3 to the cable accommodating bore 12 accommodate the wires 16 from the cable accommodating bore 12 to the respective measuring electrodes 7, where they are connected thereto by an electrically conductive adhesive, solder or the like.

A plurality of indicating means, which in this embodiment of the invention comprise light outputting means, namely, a plurality of light sources 19 are located adjacent the respective measuring electrodes 7 to produce respective light signals, in order to indicate the location of the respective measuring electrodes 7 in a vessel or lumen, the diameter, cross-sectional area and/or volume of which is to be determined or monitored. In this embodiment of the invention each light source 19 comprises one single light emitting diode 20 which is located on the corresponding measuring electrode 7. Light emanating from the light emitting diodes 20 is visible externally of the vessel or lumen through a translucent wall of the vessel or lumen. By placing an imaging device 27 of an imaging system also according to the invention and indicated generally by the reference numeral 26, which is described below with reference to FIG. 2, in a cavity of the body of the subject within which the vessel or lumen is located but externally of the vessel or lumen, an image of the vessel or lumen and the light emanating through the translucent wall of the vessel or lumen from the light emitting diodes 20 is captured by the imaging device 27. By displaying the captured image of the vessel or lumen together with the light emanating through the wall of the vessel or lumen from the light emitting diodes 20, accurate placing of the catheter in the vessel or lumen can be achieved as will be described below with reference to FIG. 2.

A radial bore 22 through each corresponding measuring electrode 7 and the catheter member 3 accommodates wires 23 from the corresponding light emitting diode 20 into the cable accommodating bore 12. The wires 23 from the light emitting diodes 20 are accommodated through the cable accommodating bore 12 to the proximal end 4 of the catheter member 3. Electrical power from a power source (not shown) adjacent the proximal end 4 of the catheter member 3 is applied to the wires 23 for powering the light emitting diodes 20.

The cable accommodating bore 12 is sealed at the proximal end 4 and the distal end 5, and the radial bores 18 and 22 are also sealed to prevent liquid from the vessel in which the catheter 1 is located entering the cable accommodating bore 12.

Figure 2:
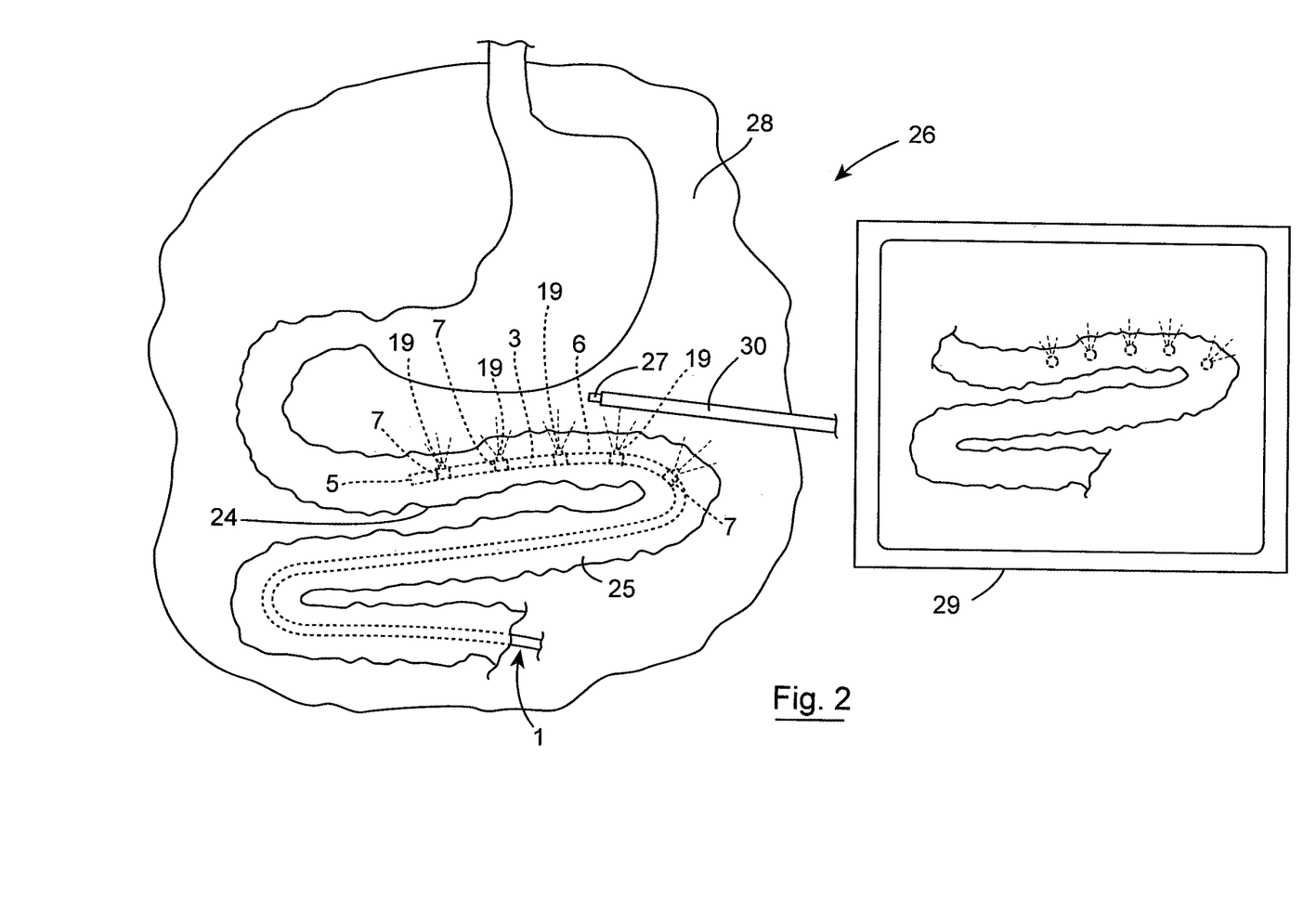
FIG. 2 is a partly cut-away perspective view of a portion of the body of a subject illustrating a portion of the catheter of FIG. 1 in use along with an imaging system also according to the invention.

Referring now to FIG. 2, the catheter 1 according to the invention is particularly suitable for use in a laparoscopic procedure where it is desired to determine the cross-sectional area, a diameter and/or the volume of a vessel or lumen in a human or animal subject, such as, a portion of a vessel or lumen, for example, a portion 24 of the intestine 25. In accordance with the invention, the imaging system 26 which comprises the imaging device 27, typically a charge coupled device (CCD) imaging chip or a video camera which is provided in a laparoscope 30 is used in conjunction with the catheter 1 for accurately locating the catheter 1 in the portion 24 of the intestine 25. The catheter 1 is initially inserted into the relevant portion 24 of the intestine 25 either orally or rectally. The imaging device 27 of the laparoscope 30 is inserted through a laparoscopic opening (not shown) formed in the wall of the abdomen, and is located in a cavity 28 within the abdomen adjacent the portion 24 of the intestine 25 but externally of the intestine 25. With the light emitting diodes 20 powered up light emitted from the light emitting diodes 20 is visible through the wall of the intestine which is translucent. The imaging device 27 captures an image of the portion 24 of the intestine 25 and the light emanating from the light emitting diodes 20 on the electrodes 7 of the catheter 1. The image captured by the imaging device 27 is displayed on a visual display screen 29 of the imaging system 26. Since the light emitting diodes 20 are located on the electrode 7 a surgeon can manoeuvre the catheter 1 within the intestine 25 while observing the image of the intestine and the light emitted from the light emitting diodes 20 on the visual display screen 29, until the catheter 1 with the electrodes 7 is accurately located in the portion 24 of the intestine 25.

Thereafter, a saline solution is delivered through the electrically conductive medium accommodating bore 10 of the catheter 1 into the portion 24 of the intestine 25. The constant current stimulating signal is applied to the stimulating electrodes 8, and the resulting voltages developed on the sensing electrodes 9 are read by a suitably programmed microprocessor (not shown) which computes the values of the transverse cross-sectional area along the portion 24 of the intestine 25 adjacent the respective sensing electrodes 9. Values of the diameter of the portion 24 of the intestine 25 may also be computed by the microprocessor from the voltage signals read from the sensing electrodes 9 if the portion 24 of the intestine 25 is assumed to be of circular transverse cross-section. From the cross-sectional area values or the diameter values, the volume of the portion 24, or a part thereof, of the intestine 25 can be computed by the microprocessor.

In use, the catheter 1 is entered through an appropriate entry point in the human or animal body with the distal end 5 as the leading end and is directed through a vessel or lumen system of the human or animal body to the vessel or lumen 25 in which the diameter, cross-sectional area and/or volume is to be determined. If the vessel or lumen 25, the diameter, cross-sectional area and/or volume of which is to be determined, is a cavity of the heart, the catheter typically is entered into the arterial system through the upper part of the leg of the subject adjacent the crotch. With the distal portion 6 of the catheter member 3 located in the vessel or lumen, the diameter, cross-sectional area and/or volume of which is to be determined, and with the imaging device 27 suitably located in the cavity of the body of the subject adjacent the vessel, but externally of the vessel, the light emitting diodes 20 are powered up to produce light.

An image of the vessel or lumen and the light emitting diodes 20 which identify the locations of the electrodes 7 is captured by the imaging device 27, and the image is displayed on the visual display screen 29 for inspection by a surgeon. The surgeon by observing the image on the visual display screen 29 can identify the location of the measuring electrodes 7 on the catheter member 3 within the vessel, and can thus manoeuvre the catheter 1 until the distal portion 6 thereof and the measuring electrodes 7 are accurately located in the vessel, the diameter, cross-sectional area and/or volume of which is to be determined. Once the distal portion 6 of the catheter member 3 and the measuring electrodes 7 are accurately located in the vessel, use and operation of the catheter 1 continues as with a conventional catheter having measuring electrodes thereon and as discussed above.

Figure 3:
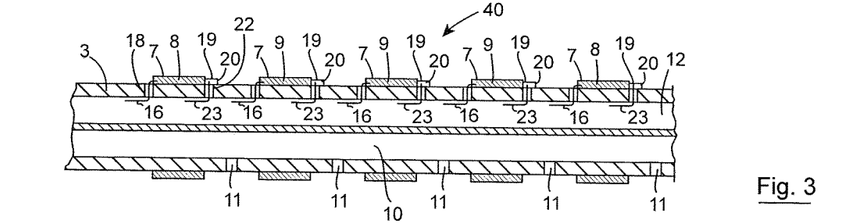
FIG. 3 is a longitudinal cross-sectional side elevational view of a portion of a catheter according to another embodiment of the invention.

Referring now to FIG. 3, there is illustrated a catheter according to another embodiment of the invention, indicated generally by the reference numeral 40 for determining the diameter, the transverse cross-sectional area and/or the volume of a vessel or lumen in the body of a human or animal subject. The catheter 40 is substantially similar to the catheter 1 and similar components are identified by the same reference numerals. The only difference between the catheter 40 and the catheter 1 is that instead of the light sources 19 being located on the measuring electrodes 7, the light sources 19, each of which comprises a single light emitting diode 20, are located on the catheter member 3 right beside the corresponding measuring electrodes 7.

Otherwise, the catheter 40 is similar to the catheter 1 and its use is likewise similar.

Figure 4:
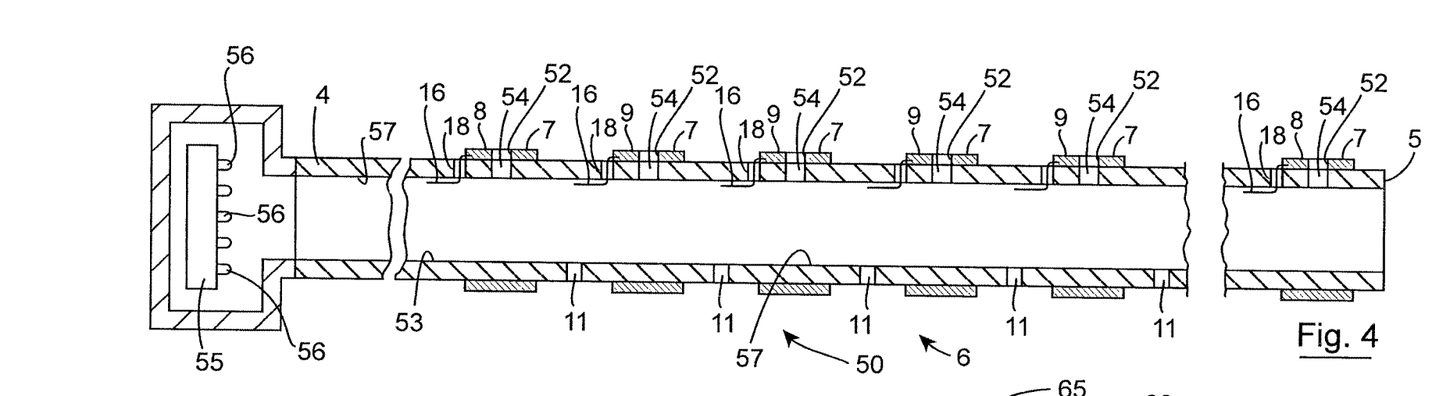
FIG. 4 is a longitudinal cross-sectional side elevational view of a catheter according to another embodiment of the invention.

Referring now to FIG. 4, there is illustrated a catheter according to another embodiment of the invention, indicated generally by the reference numeral 50 for determining the diameter, the transverse cross-sectional area and/or the volume of a vessel or lumen in the body of a human or animal subject. The catheter 50 is substantially similar to the catheter 1 and similar components are identified by the same reference numerals. The main difference between the catheter 50 and the catheter 1 is that the light outputting means of the indicating means instead of being provided by light emitting diodes as in the case of the catheters 1 and 40, the light outputting means in this embodiment of the invention are provided by a plurality of light accommodating openings 52 in the corresponding measuring electrodes 7 which communicate with a light transmitting means provided by a longitudinally extending light accommodating bore 53 through radial bores 54 extending radially through the catheter member 3. The light accommodating bore 53 extends longitudinally through the catheter member 3 from the proximal end 4 thereof to the distal portion 6 of the catheter member 3. A light source 55 in this embodiment of the invention is remotely located, and is coupled to the catheter member 3 adjacent the proximal end 4 thereof, so that light from the light source 55 is directed through the light accommodating bore 53, and in turn through the radial bores 54 and in turn through the light accommodating opening 52. The light source 55 in order to produce sufficient light comprises a plurality of light emitting diodes 56.

The light source 55 is optically coupled into the light accommodating bore 53 through a suitable light coupling means, for example, a fibre optic cable (not shown) or light reflectors (also not shown). A light directing means for directing light from the light accommodating bore 53 to and through the radial bores 54, in this embodiment of the invention comprises a reflective coating on an inner surface 57 of the light accommodating bore 53 in order to reflect light in the light accommodating bore 53 through the radial bores 54, and in turn through the light accommodating openings 52.

In this embodiment of the invention the light accommodating bore 53 may also be adapted for delivering an electrically conductive liquid therethrough to the vessel or lumen. Alternatively, a dedicated liquid medium accommodating bore extending through the catheter member 3 may be provided. In which case, separate radially extending ports would be provided from the liquid accommodating bore through which the liquid medium would be delivered to the vessel or lumen. Additionally in this embodiment of the invention the wires 16 to the measuring electrodes 7 may be accommodated through the light accommodating bore 53, or may be accommodated in a dedicated wire accommodating bore or may be accommodated through a liquid medium accommodating bore if such a bore is provided.

In use, the catheter 50 is entered into the human or animal body, and the distal portion 6 of the catheter 50 is directed into the vessel or lumen, the wall of which is translucent, and the diameter, cross-sectional area and/or volume of which is to be determined. With an imaging device similar to the imaging device 27 of the imaging system 26, which is described with reference to FIG. 2, located in a cavity of the human or animal body within which the vessel or lumen is located, but externally of the vessel or lumen, the light source 55 is powered up. An image of the vessel or lumen and the light emanating from the light accommodating openings 52, which is visible through the translucent wall of the vessel or lumen is captured by the imaging device and displayed on a visual display screen similar to that described with reference to FIG. 2. A surgeon by observing the captured image of the vessel or lumen and the light emanating from the light accommodating openings 52, which identify the locations of the corresponding electrodes 7, can manoeuvre the catheter 50 until the measuring electrodes 7 are in the desired location within the vessel or lumen, the diameter, cross-sectional area and/or volume of which is to be determined.

Otherwise, the catheter 50 and its use is substantially similar to that of the catheter 1.

Figure 5:
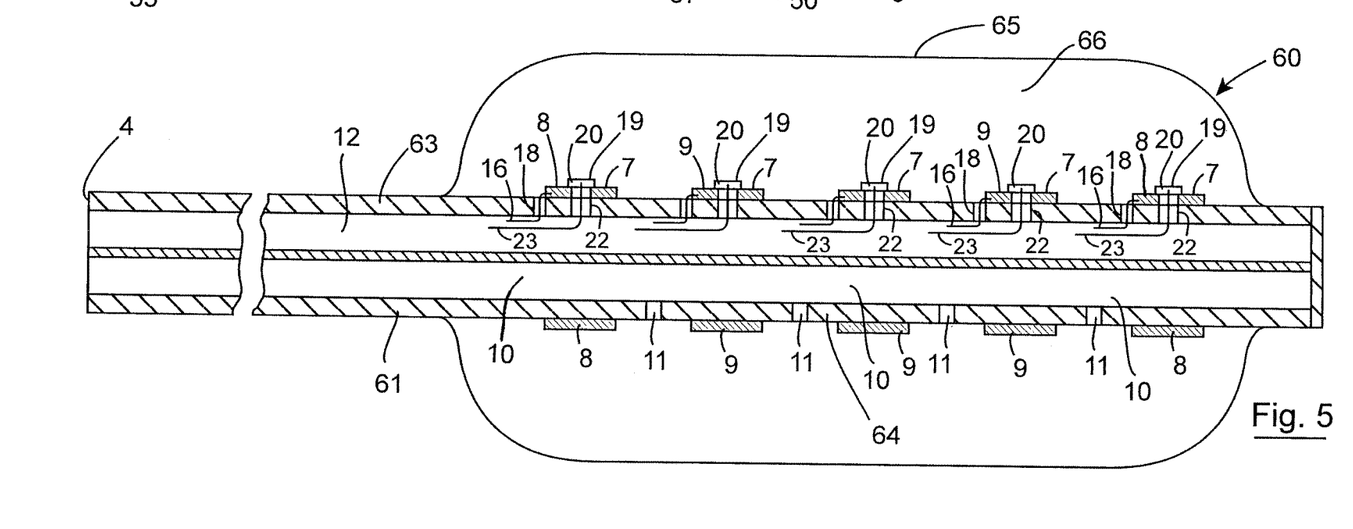
FIG. 5 is a longitudinal cross-sectional side elevational view of a balloon catheter according to another embodiment of the invention.

Referring now to FIG. 5, there is illustrated a balloon catheter also according to the invention, indicated generally by the reference numeral 60 for determining the diameter, transverse cross-sectional area and/or volume of a vessel or lumen in the body of a human or animal subject. The balloon catheter 60 is somewhat similar to the catheter 1 and where appropriate, similar components are identified by the same reference numerals. The balloon catheter 60 comprises a catheter 61 which comprises a catheter member 63 which is substantially similar to the catheter member 3 of the catheter 1. Longitudinally spaced apart measuring electrodes 7 comprising a pair of stimulating electrodes 8, and longitudinally spaced apart sensing electrodes 9 located between the stimulating electrodes 8 are located on a distal portion 64 of the catheter member 63. The electrodes 7 are band electrodes similar to the electrodes 7 of the catheter 1.

An inflatable element, in this embodiment of the invention an inflatable balloon 65 is located on the catheter member 63 adjacent the distal portion 64, and the catheter member 63 extends through the balloon 65 to define with the balloon 65 an annular hollow interior region 66. The measuring electrodes 7 are located on the distal portion 64 of the catheter member 63 within the hollow interior region 66 of the balloon 65. A communicating means comprising a longitudinally extending liquid inflating medium accommodating bore 10 similar to the liquid medium accommodating bore 10 of the catheter 1 extends longitudinally through the catheter member 63 for accommodating an electrically conductive liquid inflating medium into the hollow interior region 66 of the balloon 65 through the radial ports 11 for inflating the balloon 65.

A plurality of light outputting means, namely, single light emitting diodes 20 are mounted on the respective measuring electrodes 7 in a similar manner as the light emitting diodes 20 are mounted on the measuring electrodes 7 of the catheter 1. Wires 23 for powering the light emitting diodes 20, and wires 16 for communicating with the measuring electrodes 7 are accommodated through a cable accommodating bore 12. Radial bores 18 extending through the catheter member 63 accommodate the wires 16 to the measuring electrodes 7, while the wires 23 are accommodated through the radial bores 22 extending through the catheter member 63 and the corresponding electrodes 7 to the light emitting diodes 20.

The balloon catheter 60 according to this embodiment of the invention is particularly suitable for determining the diameter, cross-sectional area and/or the volume of a relatively large vessel, organ or lumen, for example, the oesophagus, the stomach, large intestine, rectum and the like, and is also particularly suitable for monitoring the diameter, cross-sectional area and volume of a stomach during bariatric and other such surgical procedures, as well as for monitoring the diameter of the lower oesophageal sphincter during anti-reflux surgery.

In use, the catheter 60 is entered into the vessel or lumen, the diameter, cross-sectional area or volume of which is to be determined through a suitable orifice or entry point in the body with the distal end 5 of the catheter member 63 forming the leading end of the balloon catheter 60. When the balloon 65 of the balloon catheter 60 is located in the vessel or lumen, the diameter, cross-sectional area and/or volume of which is to be determined, and with an imaging device similar to the imaging device 27 of the imaging system 26 located in a cavity in the human or animal body within which the vessel is located but externally of the vessel, the light emitting diodes 20 are powered up. The imaging device captures an image of the vessel or lumen and the light emanating from the light emitting diodes 20 through the translucent wall of the vessel. The captured image is displayed on a visual display screen similar to the visual display screen 29 of the imaging system 26 described with reference to FIG. 2. The surgeon by observing the image displayed on the visual display screen, and in particular the image of the light emitting diodes 20 which indicate the locations of the electrodes 7 relative to the vessel or lumen can manoeuvre the balloon catheter 60 until the balloon 65 and the measuring electrodes 7 are accurately located in the vessel or lumen.

Thereafter the use of the balloon catheter 60 is similar to that of a conventional balloon catheter.

Figure 6:
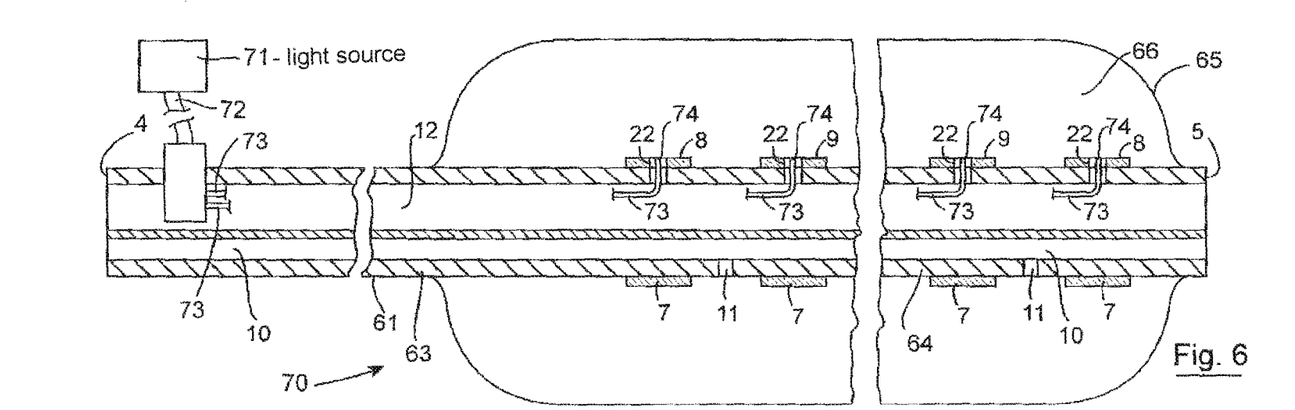
FIG. 6 is a longitudinal cross-sectional side elevational view of a balloon catheter according to a further embodiment of the invention.

Referring now to FIG. 6, there is illustrated a balloon catheter also according to the invention, indicated generally by the reference numeral 70 for determining the diameter, transverse cross-sectional area and/or volume of a vessel or lumen in the body of a human or animal subject. The balloon catheter 70 is substantially similar to the balloon catheter 60 and similar components are identified by the same reference numerals. The main difference between the balloon catheter 70 and the balloon catheter 60 is that instead of the light outputting means of the indicating means comprising light emitting diodes located on the electrodes, a remote light source 71 is provided remotely of the balloon catheter 70. Light from the remote light source 70 is optically coupled to the proximal end 4 of the catheter member 63 by an optical fibre cable 72. Optical fibres 73, which are optically coupled to the optical fibre cable 72 adjacent the proximal end 4 of the catheter member 63, extend through the bore 12, which extends through the catheter member 63, and terminate in distal ends 74 in the radial bores 22 which extend through the catheter member 63 and through the measuring electrodes 7. The distal ends 74 of the optical fibres 73 direct light from the remote light source 71 radially from the catheter member 63 through the radial bores 22.

In this embodiment of the invention the light source 71 is provided by a single remote light source, which may comprise one or a plurality of light emitting diodes, to which the optical fibre cable 72 is optically coupled for collecting light from the light source 71.

In use, when the balloon 65 is located in the vessel or lumen, the diameter, cross-sectional area and/or the volume of which is to be determined, the remote light source 71 is powered up. Light from the light source 71 is transmitted through the optical fibre cable 72, and in turn through the optical fibres 73 to emanate radially from the catheter member 3 through the radial bores 22 to identify the locations of the electrodes 7. An imaging device similar to the imaging device 27 of the imaging system 26 described with reference to FIG. 2 located in a cavity within which the vessel or lumen is located, but externally of the vessel or lumen captures an image of the vessel or lumen and the light emanating through the translucent wall of the vessel or lumen from the distal ends 74 of the optical fibres 73. The captured image is displayed on a visual display screen similar to the visual display screen 29 of the imaging system 26 described with reference to FIG. 2. A surgeon by observing the image on the visual display screen identifies the locations of the electrodes 7 from the displayed image of the light emanating from the distal ends 74 of the optical fibres 73, and can manoeuvre the balloon catheter 70 until the balloon 65 and the measuring electrodes 7 are accurately located in the vessel or lumen.

Thereafter, use of the balloon catheter 70 is similar to use of a conventional balloon catheter.

Figure 7:
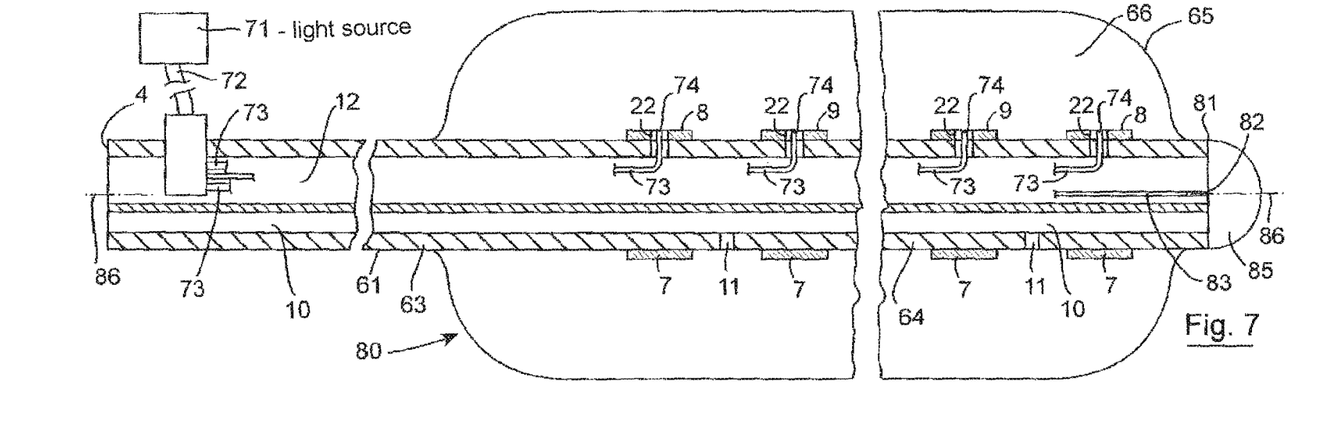
FIG. 7 is a longitudinal cross-sectional side elevational view of a balloon catheter according to a further embodiment of the invention.

Referring now to FIG. 7, there is illustrated a balloon catheter according to another embodiment of the invention, indicated generally by the reference numeral 80 for determining the diameter, transverse cross-sectional area and/or the volume of a vessel or lumen in the body of a human or animal subject. The balloon catheter 80 is substantially similar to the balloon catheter 70 of FIG. 6, and similar components are identified by the same reference numerals. The main difference between the balloon catheter 80 and the balloon catheter 70 is that as well as comprising indicating means provided by light outputting means, which in this embodiment of the invention are provided by light emanating from the distal ends 74 of the optical fibres 73, the balloon catheter 80 also comprises an indicating means for identifying another known location of the balloon catheter, namely, a distal leading tip 81 of the catheter member 63. In this embodiment of the invention this indicating means comprises a light outputting means which identifies the leading distal tip 81 of the catheter member 63 and comprises light from a distal terminal end 82 of an optical fibre 83. The optical fibre 83 is optically coupled to the optical fibre cable 72 adjacent the proximal end 4 of the catheter member 63. In this embodiment of the invention the distal leading tip 81 of the catheter member 63 terminates in a hemispherical lens 85 which is optically coupled to the distal terminal end 82 of the optical fibre 83 in order that light emanating from the distal terminal end 82 of the optical fibre 83 is diffused adjacent the distal leading tip 81 of the catheter member 63. The lens 85 diffuses the light from the optical fibre 83 through an angle of 360° around a longitudinally extending central axis 86 defined by the catheter member 63, and also through an angle of 180° relative to the longitudinally extending central axis 86 of the catheter member 63.

In use, the balloon catheter 80 is entered through an appropriate entry orifice of the subject and the balloon 65 is located in the vessel or lumen, the diameter, cross-sectional area and/or volume of which is to be determined. The remote light source 71 is powered up. An imaging device of an imaging system similar to the imaging system 26 described with reference to FIG. 2 located in a cavity of the human or animal body adjacent but externally of the vessel or lumen sequentially captures an image of the vessel and the light emanating through the translucent wall of the vessel or lumen from the distal ends 74 of the optical fibres 73 and from the lens 85 at the distal leading tip 81 of the catheter member 63. The captured image of the vessel or lumen and the light emanating from the distal ends 74 of the optical fibres 73 and from the lens 85 is displayed on a visual display screen. A surgeon by observing the image of the light emanating from the distal ends 74 of the optical fibres 73 and from the lens 85 which identify the locations of the electrodes 7 and the distal leading tip 81, respectively, of the catheter member 63 can manoeuvre the balloon catheter 80 so that the distal leading tip 81 of the catheter member 63 and the electrodes 7 thereof are accurately located in the vessel or lumen.

Thereafter use of the balloon catheter 80 in determining the diameter, transverse cross-sectional area and/or volume of the vessel is as described with reference to the balloon catheter 60 of FIG. 5 and the catheter 1 of FIG. 1.

Figure 8:
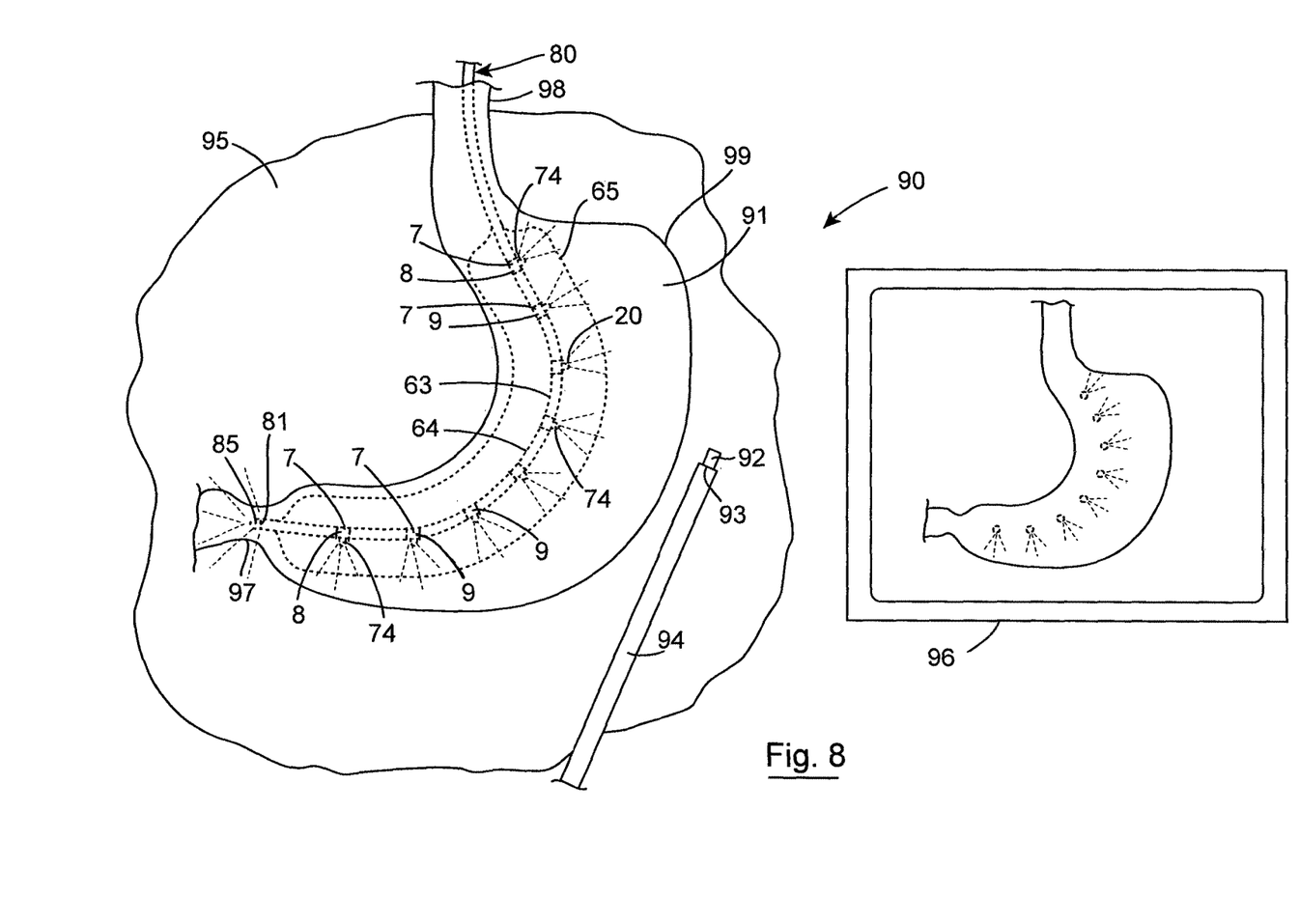
FIG. 8 is a partly cut-away perspective view of a portion of the body of a subject illustrating a portion of the balloon catheter of FIG. 7 in use along with an imaging system also according to the invention.

Referring now to FIG. 8 there is illustrated an imaging system 90 according to the invention for use in a bariatric surgical procedure being carried out on a stomach 91 of a subject. Any one of the balloon catheters 60, 70 or 80 may be used in the bariatric surgical procedure. However, in this embodiment of the invention the balloon catheter 80 is being used. The imaging system 90 comprises an imaging chip 92 which is integrated onto a distal end 93 of a laparoscope 94 which is inserted into an abdominal cavity 95 of the subject adjacent but externally of the stomach 91 for capturing an image of the stomach 91 externally thereof and the light emanating from the distal ends 74 of the optical fibres 73 and the lens 85 through the wall 99 of the stomach which is translucent. A visual display screen 96 displays the image captured by the imaging chip 92 of the stomach 91 and the light from the distal ends 74 of the optical fibres 73 and the lens 85, which are processed through a microprocessor (not shown) prior to being displayed on the visual display screen 96.

In use, the laparoscope 94 with the imaging chip 92 on the distal end 93 thereof is inserted through a laparoscopic opening into the abdominal cavity 95 and manoeuvred therein so that an image of the stomach 91 is captured by the imaging chip 92. The balloon catheter 80 is inserted orally through the oesophagus 98 to the stomach 91. As the balloon catheter 80 is being inserted into the stomach 91 the remote light source 71 is powered up and light from the light source 71 is transmitted through the optical fibres 73 and the optical fibre 83 and is outputted through the distal ends 74 of the optical fibres 73 and through the lens 85 at the distal leading end 81 of the catheter member 63 of the balloon catheter 80. Since the wall 99 of the stomach 91 is translucent, light emanating from the distal ends 74 of the optical fibres 73, and from the lens 85 is simultaneously captured by the imaging chip 92 with the captured image of the stomach 91. The image which is captured by the imaging chip 92 is displayed on the visual display screen 96, thereby allowing a surgeon inserting a balloon catheter 80 into the stomach 91 to observe the progress of the distal portion 64 of the catheter member 3 through the stomach 91. The surgeon by observing the displayed image on the visual display screen 96 can manoeuvre the balloon catheter 80 until the lens 85 is accurately located in the pylorus 97 and the distal portion 64 of the catheter member 63 of the balloon catheter 80 is correctly located in the stomach 91.

Once the balloon catheter 80 has been correctly located in the stomach 91, the balloon 65 of the balloon catheter 80 is inflated with a saline solution to the desired diameter so that the bariatric surgical procedure can commence. Thereafter the bariatric procedure is carried out in a conventional manner.

Figure 9:
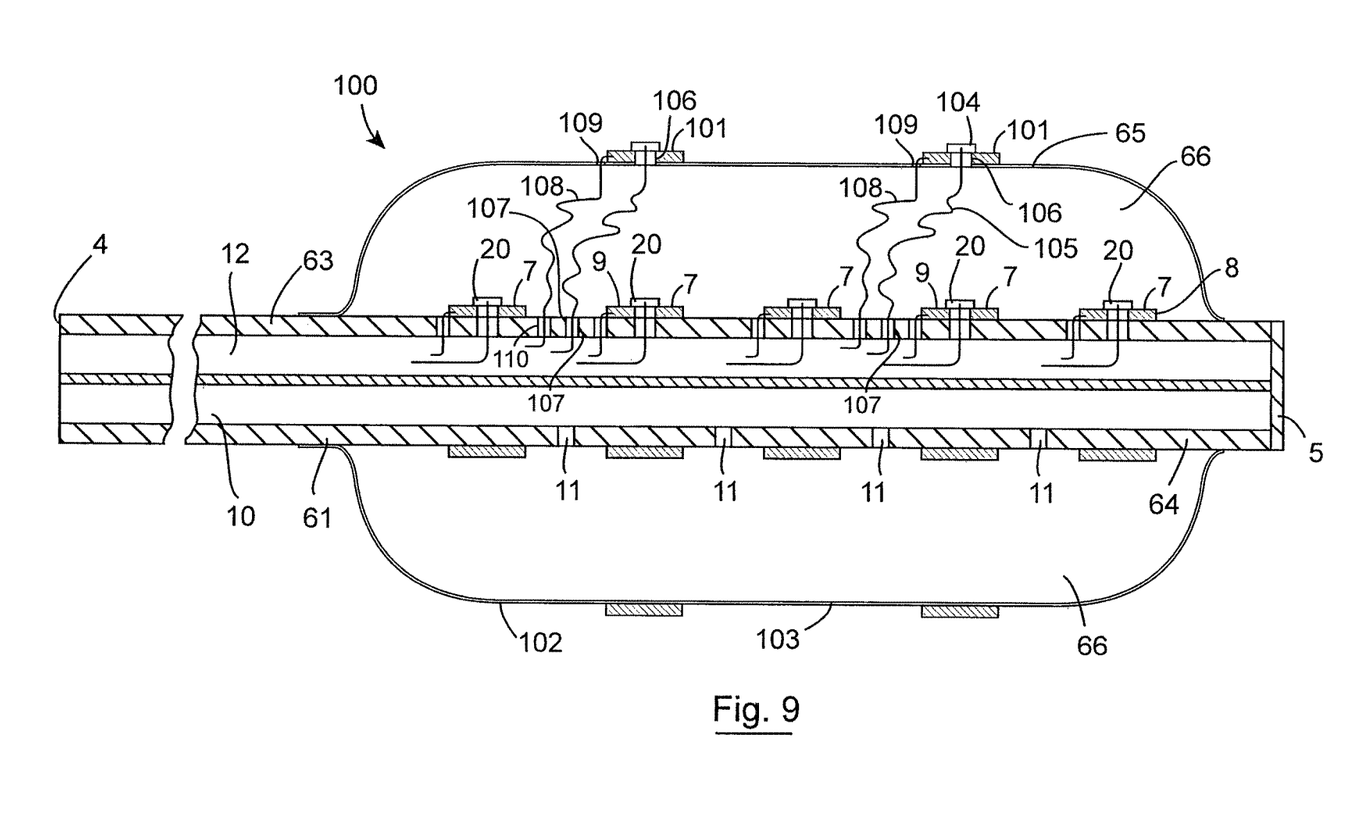
FIG. 9 is a longitudinal cross-sectional side elevational view of a balloon catheter according to a further embodiment of the invention.

Referring now to FIG. 9 there is illustrated a balloon catheter according to another embodiment of the invention indicated generally by the reference numeral 100 for ablating tissue in a vessel, lumen or organ in the body of a human or animal subject. The balloon catheter 100 is substantially similar to the balloon catheter 60 described with reference to FIG. 5, and similar components are identified by the same reference numerals. The main difference between the balloon catheter 100 and the balloon catheter 60 is that a pair of ablating electrodes 101 are located on an outer surface 102 of a member 103 of the balloon 65 of the balloon catheter 100 for ablating tissue to be ablated from the vessel lumen or organ. The ablating electrodes 101 are band electrodes and extend around the outer surface 102 of the membrane 103 of the balloon 65, and are of an electrically conductive material which is expandable, to expand with expansion of the membrane 103 of the balloon 65. Indicating means for indicating the location of the ablating electrodes 101 in the vessel, lumen or organ in this embodiment of the invention comprise respective light emitting diodes 104 which are mounted on the ablating electrodes 101. Electrically conductive wires 105 extending through bores 106 which extend through the corresponding ablating electrodes 101 and the membrane 103 of the balloon 65 provide power to the corresponding light emitting diodes 104. The wires 105 are accommodated into the cable accommodating bore 12 in the catheter member 63 through radially extending bores 107 in the catheter member 63. The wires 105 are accommodated through the cable accommodating bore 12 to the proximal end 4 of the catheter member 63 where they are coupled to a suitable remote power source (not shown).

Electrically conductive wires 108 extending through bores 109 which extend through the membrane 103 of the balloon 65 power the ablating electrodes 101. The wires 108 are accommodated into the cable accommodating bore 12 of the catheter member 63 through radially extending bores 110 in the catheter member 63. The wires 108 are accommodated through the cable accommodating bore 12 to the proximal end 4 of the catheter member 63 where they are connected to a suitable remote power supply (not shown).

The length of the wires 105 and 108 extending from the bores 107 and 110 to the light emitting diodes 104 and the ablating electrodes 101, respectively, are of sufficient length to accommodate inflating and expansion of the balloon 65 to fill the vessel or lumen from which tissue is to be ablated.

Measuring electrodes 7 are located on the distal portion 64 of the catheter member 63 within the hollow interior region 66 of the balloon 65 for determining the diameter, transverse cross-sectional area and/or volume of the balloon 65 when inflated with an electrically conductive liquid medium, and in turn for determining the diameter, transverse cross-sectional area and/or volume of the vessel or lumen or organ within which the balloon 65 is inflated. Indicating means provided by light emitting diodes 20 similar to the light emitting diodes 20 of the balloon catheter 60 of FIG. 5 are located on the measuring electrodes 7, in a similar manner as on the measuring electrode 7 of the balloon catheter 60. The powering of the light emitting diodes 20 is similar to that described with reference to the balloon catheter 60.

In use, the balloon catheter 100 is appropriately inserted into the body of the subject with the balloon 65 located in the vessel, lumen or organ from which tissue is to be ablated. An imaging device similar to the imaging device 27 of the imaging system 26 described with reference to FIG. 2 is inserted into a cavity within which the vessel, lumen or organ, and is located externally of the vessel, lumen or organ. The electrodes 20 are powered up. An image of the vessel, lumen or organ and the light emanating through a translucent wall of the vessel, lumen or organ from the light emitting diodes 20 is captured by the imaging device 27 and displayed on a visual display screen, similar to the visual display screen 29 of the imaging system 26 described with reference to FIG. 2. While observing the image displayed on the screen, the balloon catheter 100 is manoeuvred in the vessel, lumen or organ for locating the distal portion 64 of the catheter member 63 and the balloon 65 in a desired location therein. With the balloon 65 accurately located in the vessel, lumen or organ, the balloon 65 is inflated with the electrically conductive liquid inflating medium until the balloon 65 is of the desired diameter to fill the transverse cross-sectional area of the vessel, lumen or organ. The light emitting diodes 104 are then powered up. An image of the vessel, lumen or organ and the light emanating through the translucent wall of the vessel, lumen or organ from the light emitting diodes 104 is captured by the imaging device and displayed on the visual display screen. While observing the image displayed on the screen, the balloon catheter 100 can then be further manoeuvred within the vessel, lumen or organ until the ablating electrodes 101 are correctly and accurately aligned with the tissue in the vessel, lumen or organ to be ablated. Thereafter ablating of the tissue is carried out in a conventional manner.

It will of course be appreciated that the light emitting diodes 104 can be powered up simultaneously with the light emitting diodes 20, and the manoeuvring of the balloon catheter 100 in the vessel, lumen or organ in order to correctly position the balloon 65 and the ablating electrodes 101 therein could be carried out in one manoeuvring of the balloon catheter 100 within the vessel, lumen or organ.

While the light outputting means have been described as being provided by light emitting diodes located on or adjacent the measuring electrodes, and also by light emanating from openings in the catheter and electrodes and from the terminal ends of optical fibres, any other suitable light outputting means may be provided in order to produce a signal indicative of the locations of all or some or one of the measuring electrodes. It will also be appreciated that more than one light outputting means may be provided corresponding to each measuring electrode, and in which case, it is envisaged that the light outputting means of each measuring electrode would be located at circumferentially spaced apart intervals around the electrode or around the catheter adjacent the electrode.

It is also envisaged that where the light outputting means comprises an opening formed in the respective electrodes or formed by an opening in the catheter member adjacent each electrode, it is envisaged that a lens may be provided in the opening for focusing the light being outputted through the opening. Indeed, it is envisaged that where light is being transmitted from a light source by one or more optical fibres to emanate from a distal end of each optical fibre through the opening formed in the electrode or in the catheter member adjacent the electrode, a lens may also be provided in such an opening for focusing light being emitted by the distal end of each optical fibre.

Where the light transmitting means comprises optical fibres for transmitting light from a light source to locations adjacent the electrodes and/or the distal leading tip of the catheter, it is envisaged in certain cases that each optical fibre may be accommodated in a separate corresponding bore extending longitudinally through the catheter member.

Needless to say, the light outputting means may be located in any suitable location on or adjacent the measuring electrodes.

It is also envisaged that while it is desirable to provide a light outputting means on each measuring electrode, in certain cases, it is envisaged that light outputting means may only be provided adjacent the sensing electrodes, and in certain cases, only adjacent some of the sensing electrodes, or alternatively, adjacent one or both of the stimulating electrodes.

Additionally, it is envisaged that in order to identify specific ones of the electrodes, the light outputting means may be adapted to emit light of different colours, different wavelengths or the like, so that each or some of the measuring electrodes or ablating electrodes, as the case may be, may be identified by the specific colour or wavelength of the light emitted by the corresponding light outputting means, for example, the measuring electrodes may be identified by one or more colours, and the ablating electrodes may be identified by one or more different colours which would be different to the colour or colours of the light used to identify the measuring electrodes.

However, where the light outputting means are adapted to produce light of different colours or of different wavelengths, it is envisaged that the light emitting means will be provided by respective light sources located on or adjacent the electrodes, or by corresponding optical fibres which would be coupled remotely to light sources of the respective different colours and/or wavelengths. In which case, it is envisaged that separate bores may be provided extending through the catheter for accommodating optical fibres which transmit light of different colours or different wavelengths. Needless to say, where the light of different colours or different wavelengths is transmitted through longitudinally extending light accommodating bores, it is envisaged that separate light accommodating bores will be provided for light of respective different colours.

While the light emitting means have been described as producing visible light, it is envisaged in certain cases that the light emitting means may be adapted to produce light outside the visible spectrum, for example, infra-red light, ultra-violet light or the like. It is also envisaged that indicating means other than light emitting means may be provided, for indicating the locations of the electrodes. For example, such indicating means could be adapted to produce signals other than light signals, for example, ultrasonic signals, microwave signals, electro-magnetic signals or the like which could be received by a suitable receiving means located externally of the vessel or lumen, the diameter, cross-sectional area and/or volume of which is to be determined.

In which case signals from the receiving means and the imaging device would be mixed in a suitably programmed microprocessor, and the captured images would be displayed along with images of the locations of the catheter member from which the signals are transmitted.

While only the balloon catheter of FIG. 7 has been described as comprising an indicating means for identifying the distal leading tip of the catheter member, it will be appreciated that the catheter members of any of the catheters and balloon catheters described with reference to FIGS. 1 to 6 and 9 may be provided with an indicating means for indicating the distal leading tip of the catheter member thereof. Needless to say, the indicating means may comprise a light outputting means which may be provided by the terminal end of an optical fibre, a lens, or indeed by a light emitting diode, or any other suitable light outputting means, or any other suitable indicating means located adjacent the distal leading tip of the catheter member.

It is also envisaged that while the measuring electrodes have been described as being band electrodes which extend completely around the catheter member, any other suitable electrodes may be used, and needless to say, it will be appreciated that where band electrodes are used, the bands need not extend completely around the catheter member. Indeed, in certain cases, it is envisaged that where the electrodes do not extend completely around the catheter member, the light emitting means may be located on the catheter member in a gap between respective opposite ends of the electrode.

It will also be appreciated that while the catheters have been described as being adapted for measuring diameter, transverse cross-sectional area and/or volume of a vessel or lumen, the catheters may be provided for ablating tissue, and in which case, one or more electrodes would be provided on the catheter member in order to carry out ablating of the tissue. In which case, an indicating means, such as a light emitting means would be provided adjacent each ablating electrode.

While in the catheters and balloon catheters described with reference to FIGS. 1 to 9, the locations which are identified by indicating means are either one or more of the measuring electrodes and/or the distal leading tip of the catheter member, it will be appreciated that the indicating means may be adapted to identify any suitable known location on a catheter member or a balloon of a balloon catheter as well as, one or more of the measuring electrodes and/or the distal leading tip of the catheter member.

It will also be appreciated that while in the embodiments of the catheters and balloon catheters which have been described with reference to FIGS. 1 to 9 have been described as comprising a light outputting means located adjacent each of the electrodes on the catheter, in certain cases it is envisaged all the electrodes will not be provided with indicating means, and in some cases, it is envisaged that in the case of a catheter or a balloon catheter with measuring electrodes, only the two outer electrodes would be provided with an indicating means, in other words, the two stimulating electrodes would be provided with indicating means, while the other electrodes would not be provided with indicating means. Alternatively, as well as the stimulating electrodes being provided with indicating means some of the sensing electrodes may also be provided with indicating means, for example, a central one of the sensing electrodes may be provided with an indicating means. Similarly, in the case of a catheter or a balloon catheter with ablating electrodes, indicating means may be provided in conjunction with only one or some of the ablating electrodes, for example, the outer electrodes may only be provided with indicating means.

While the catheters and balloon catheters have been described for measuring transverse cross-sectional area, diameter and/or volume of a vessel, lumen or organ using impedance measurements, it will be appreciated that the catheters and balloon catheters may be used for making impedance measurements in general, and not just measurements of diameter, transverse cross-section and volume. For example, the catheters and balloon catheters may be used as electrophysiology catheters and balloon catheters which measure heart signals.

While the balloon catheters, and in particular the ablating balloon catheter of FIG. 9, have been described as comprising measuring electrodes located on the catheter member within the balloon, it is envisaged that the ablating balloon catheter may be provided without such measuring electrodes. In which case, it will be appreciated that any suitable inflating medium besides an electrically conductive inflating medium may be provided for inflating the balloon.

It will also be appreciated that any other suitable directing means for directing light in the light accommodating bore extending through the catheter member from the light accommodating bore through the bores 54 in the catheter member and through the openings 52 in the measuring electrodes besides providing a reflective coating on the inner surface of the light accommodating bore. For example, it is envisaged that reflectors, refractors or the like may be located in the light accommodating bore adjacent or opposite the radial bores 54, and such reflectors, refractors, or the like would be suitably angled for directing light from the light accommodating bore through the radial bores 54 and in turn the openings 52 in the corresponding electrodes.

The invention claimed is:

1. A catheter comprising:
   an elongated catheter member,
   a plurality of spaced apart band electrodes located on the catheter member, and
   an indicating means comprising a light source adapted to output a detectable light signal, and a light outputting means provided by a light accommodating bore extending through at least one of the band electrodes for accommodating the detectable light signal therethrough for identifying the location of the corresponding band electrode.

2. A catheter as claimed in claim 1 in which the signal outputted by the indicating means is adapted to be receivable by an imaging device of an imaging system.

3. A catheter as claimed in claim 1 in which a corresponding light source is provided for each light accommodating bore.

4. A catheter as claimed in claim 1 further comprising an inflatable balloon mounted on the catheter member, and a communicating means being provided for communicating the balloon with an inflating medium source, at least one of the band electrodes being located on the balloon on an outer surface, thereof and having one of the light accommodating bores extending therethrough.

5. A catheter as claimed in claim 4 in which the balloon is located on the catheter member with the electrodes located on the catheter member within the balloon.

6. A catheter as claimed in claim 1 in which each electrode is provided with a corresponding light accommodating bore.

7. A catheter as claimed in claim 1 in which the light source comprises a light emitting diode.

8. A catheter as claimed in claim 1 in which a plurality of light sources are provided, and at least some of the light sources produce light of respective different wavelengths.

9. A system for locating a catheter in a vessel or lumen in a human or animal subject, the system comprising:
   a catheter locating in the vessel or lumen, the catheter comprising:
      an elongated catheter member, a plurality of spaced apart electrodes located on the catheter member, and an indicating means comprising a light source adapted to output a detectable light signal, and a light outputting means provided by a light accommodating bore extending through at least one of the electrodes for accommodating the detectable light signal therethrough for identifying the location of the corresponding electrode, and an imaging device adapted for locating in the body of the subject adjacent the vessel or lumen but exteriorly thereof, the imaging device being adapted for capturing an image of the vessel or lumen and the detectable light signal outputted through the light accommodating bore of the at least one electrode of the catheter member located within the vessel or lumen.

10. A system as claimed in claim 9 in which the imaging device comprises a charge coupled device (CCD) imaging chip.

11. A system as claimed in claim 9 in which the imaging device comprises a video camera.

12. A system as claimed in claim 9 in which the imaging device is adapted for use in a laparoscopic procedure.

13. A method for locating a catheter in a vessel or lumen of a human or animal subject, the catheter comprising a catheter member and a plurality of longitudinally spaced apart electrodes located on the catheter member, the method comprising forming a light accommodating bore extending through at least one of the electrodes, providing an indicating means in the form of a light source to output a detectable light signal through the light accommodating bore of the at least one electrode, placing a portion of the catheter member with the electrodes in the vessel or lumen, placing an imaging device in the body of the subject adjacent the vessel or lumen but exteriorly of the vessel or lumen, causing the light source to output the detectable light signal, and operating the imaging device to capture an image of the vessel or lumen and the detectable light signal for in turn detecting the location of the electrode accommodating the detectable light signal therethrough in the vessel or lumen.

14. A method as claimed in claim 13 in which the capture image is displayed on a visual display screen.

15. A method as claimed in claim 13 in which the catheter member is manoeuvred within the vessel or lumen until the captured image of the vessel or lumen and the detectable light signal outputted through the electrode displayed on the visual display screen is indicative of the catheter member being correctly located in the vessel or lumen.

16. A method as claimed in claim 13 in which the imaging device comprises one of a video camera and a charge coupled device (CCD) imaging chip.

17. A catheter comprising:

an elongated catheter member, a plurality of spaced apart electrodes located on the catheter member, at least some of the electrodes being adapted for measuring volume and/or transverse cross-sectional area of a vessel or a lumen in which the catheter is located, two of the electrodes being located longitudinally spaced apart from each other on a distal portion of the catheter member and being adapted as stimulating electrodes for receiving a stimulating electrical current, and other ones of the electrodes being located on the catheter member between the stimulating electrodes longitudinally spaced apart from each other and from the stimulating electrodes, and being adapted as sensing electrodes for sensing a voltage developed thereon in response to a stimulating current being applied to the stimulating electrodes when the distal portion of the catheter member is located in a an electrically conductive medium, and an indicating means comprising a light source adapted to output a detectable light signal, and a light outputting means provided by a light accommodating bore extending through at least one of the electrodes for accommodating the detectable light signal therethrough for identifying the location of the corresponding electrode.

18. A catheter comprising:

an elongated catheter member, an indicating means comprising a light source adapted to output a detectable light signal, and a plurality of spaced apart electrodes located on the catheter member, each electrode comprising a light outputting means provided by a light accommodating bore extending through the electrode for accommodating the detectable light signal therethrough for identifying the location of the corresponding electrode.

* * * * *